United States Patent [19]

Parsons

[11] Patent Number: 4,913,699
[45] Date of Patent: Apr. 3, 1990

[54] DISPOSABLE NEEDLELESS INJECTION SYSTEM

[76] Inventor: James S. Parsons, 23875 Longspur Ct., Laguna Niguel, Calif. 92677

[21] Appl. No.: 167,337
[22] Filed: Mar. 14, 1988
[51] Int. Cl.⁴ .............................................. A61M 5/30
[52] U.S. Cl. ........................................ 604/68; 604/70
[58] Field of Search ........................ 604/68, 69, 70, 71, 604/140, 141

[56] References Cited

U.S. PATENT DOCUMENTS

| | | |
|---|---|---|
| Re. 24,419 | 1/1958 | Ziherl et al. . |
| 2,547,099 | 4/1951 | Smoot . |
| 2,605,763 | 8/1952 | Smoot . |
| 2,635,601 | 4/1953 | May . |
| 2,645,223 | 7/1953 | Lawshe et al. . |
| 2,650,591 | 9/1953 | Love . |
| 2,691,374 | 10/1954 | McKibben et al. . |
| 2,699,166 | 1/1955 | Dickinson, Jr. et al. . |
| 2,704,543 | 3/1955 | Scherer . |
| 2,737,946 | 3/1956 | Hein, Jr. . |
| 2,764,977 | 10/1956 | Ferguson . |
| 2,800,903 | 7/1957 | Smoot . |
| 2,821,193 | 1/1958 | Ziherl et al. . |
| 2,821,981 | 2/1958 | Ziherl et al. . |
| 3,045,659 | 7/1962 | Malcolm . |
| 3,057,349 | 10/1962 | Ismach . |
| 3,115,133 | 12/1963 | Morando . |
| 3,131,692 | 5/1964 | Love . |
| 3,138,157 | 6/1964 | Ziherl et al. . |
| 3,202,151 | 8/1965 | Kath . |
| 3,292,621 | 12/1966 | Banker . |
| 3,292,622 | 12/1966 | Banker . |
| 3,378,007 | 4/1968 | Poulsen . |
| 3,461,867 | 8/1968 | Zimmet et al. . |
| 3,464,412 | 9/1969 | Schwartz . |
| 3,668,765 | 9/1972 | Gasaway . |
| 3,695,266 | 10/1972 | Lussier . |
| 3,714,943 | 2/1973 | Yanof et al. . |
| 3,788,315 | 1/1974 | Laurens . |
| 3,805,783 | 4/1974 | Ismach . |
| 3,815,594 | 6/1974 | Doherty . |
| 3,853,125 | 12/1974 | Clarke et al. . |
| 3,859,996 | 1/1975 | Mizzy et al. . |
| 3,908,651 | 9/1975 | Fudge . |
| 3,933,155 | 1/1976 | Johnston . |
| 3,945,379 | 3/1976 | Pritz et al. . |
| 3,945,383 | 3/1976 | Bennett et al. . |
| 4,004,575 | 1/1977 | Sarsedt . |
| 4,031,889 | 6/1977 | Pike . |
| 4,059,107 | 11/1977 | Iriguchi et al. . |
| 4,089,334 | 5/1978 | Schewbel et al. . |
| 4,103,684 | 8/1978 | Ismach . |
| 4,124,024 | 11/1978 | Schewbel et al. . |
| 4,128,098 | 12/1978 | Bloom et al. . |
| 4,301,795 | 11/1981 | Zimmerman . |
| 4,329,988 | 5/1982 | Sarnof et al. . |
| 4,342,310 | 8/1982 | Lindmayer et al. . |
| 4,400,172 | 8/1983 | Dettbarn et al. . |
| 4,403,609 | 9/1983 | Cohen . |
| 4,403,989 | 9/1983 | Christensen et al. . |
| 4,421,508 | 12/1983 | Cohen . |
| 4,475,905 | 9/1984 | Himmelstrup . |
| 4,518,385 | 5/1985 | Lindmayer et al. . |
| 4,592,742 | 6/1986 | Landau . |
| 4,596,556 | 6/1986 | Morrow et al. . |
| 4,680,027 | 7/1987 | Parsons et al. . |

Primary Examiner—John D. Yasko
Attorney, Agent, or Firm—Gordon L. Peterson; Loyal M. Hanson

[57] ABSTRACT

A needleless injector device includes an integral unit that is dimensioned and arranged to be grasped in the hand of a user, loaded with a selected dosage, and held proximate the skin in order to inject the selected dosage in a high pressure jet sufficient to pass the selected dosage through the skin for injection purposes, the unit having a barrel portion, a gas storage portion, and an intermediate portion. A trigger operates a release mechanism to release compressed gas from a storage compartment to act upon a piston and drive a plunger that ejects the selected dosage of medication through an aperture in the discharge end of the barrel portion, the piston face being larger than the plunger face to increase pressure. A dose dispenser combines with the injection device in a system adapted for use with an insulin or other conventional vial and the dose dispenser may include a vial adapter or the combination of a vial coupler and a transporter/loader device designed to pierce the self-sealing lid on the vial and to facilitate more precise dosage transfers.

44 Claims, 4 Drawing Sheets

DISPOSABLE NEEDLELESS INJECTION SYSTEM

BACKGROUND OF THE INVENTION

1. Technical Field

This invention relates generally to hypodermic injection devices, and more particularly to needleless injection devices that avoid piercing the skin by utilizing a high pressure jet to pass the medication or other substance through the skin.

2. Background Information

Needleless injection devices reduce the relative risk and discomfort of puncturing the epidermis with a hypodermic needle. In addition, they are more easily used by persons of limited skill. Thus, their use has become of increasing interest, particularly by such users as those having frequent insulin injections.

One existing needleless injection device is described in U.S. Pat. No. 4,680,027 to Parsons et al. It employs a disposable syringe that is filled by the user with a selected amount of medication. Then a separate power supply mechanism is attached to the instrument and triggered to drive a plunger against the medication. This produces a high pressure jet for injection purposes.

Although effective in many respects, the separate power supply mechanism reduces the portability and convenience of the Parsons device. Consequently, it is desirable to have a needleless injection system that overcomes this concern.

U.S. Pat. No. 4,596,556 describes a hypodermic injection apparatus having a spring-loaded firing mechanism that operates to release $CO_2$ from a capsule. This propels the capsule and a plunger toward a discharge aperture to discharge medication through the aperture. However, in being self-cocking, reloadable, and reuseable the device is somewhat complicated.

U.S. Pat. No. 3,688,765 describes another device that is intended for portable use. However, it uses a syringe in the form of a prefilled, sealed ampoule that precludes dosage selection at the time of use. In addition, the detachable syringe, disposable $CO_2$ unit, and re-usable pressurizing unit represent three separate components with which the user must contend. Consequently, it is desirable to have an injection system that overcomes these concerns also.

In this regard, it is desirable to have a pre-sterilized, disposable device for single injection use that has its own power source while being small and light enough for the user to carry along during the day. The device should be such that the user can fill it with a selected dosage conveniently and accurately from existing medication vials, and it should be conveniently and safely operated without the need to cock a spring as the source of power.

SUMMARY OF THE INVENTION

This invention solves the problems outlined above with a disposable, single-shot, needleless injection doses to the transporter/loader, and then detaches the transporter/loader from the vial coupler, carrying it along with one or more injectors until needed.

Then, when it is time for an injection, the user transfers a selected dosage from the transporter/loader to one of the injectors, positions the discharge end of the injector barrel adjacent the skin, and actuates a trigger to fire it. Compressed $CO_2$ stored in a rearward compartment powers the pre-sterilized injector to eject the selected dosage in a high pressure jet through an aperture in the discharge end of the injector barrel. This injects the medication.

With the injection completed, the injector is discarded while the transporter/loader device is retain for further use. Use of the vial adapter device is somewhat similar, but it has no transportable section. Instead, it is just a single unit that remains attached to the vial. Operation of a valve arrangement enables withdrawal of medication from the vial in one valve position and loading into the ejector device in another valve position.

Composed of a thermoplastic material, the injector may include a graduated scale on the barrel that facilitates precise dosage transfer and a safety lock on the trigger that inhibits accidental discharge. Thus, the injector is a lightweight, portable, disposable, and self-contained device that combines with the vial coupler and the transporter (or the single unit vial adapter) to device that can be loaded with a selected dosage. In addition, a dose dispenser is provided to relieve the user of the need to manipulate a hypodermic needle in order to pierce the self-sealing lid of a vial each time medication is to be withdrawn. The dose dispenser attaches permanently to the vial to provide needleless access, and it combines with the injection device in a system that greatly facilitates the self-administration of medication.

The dose dispenser may include the combination of a transporter/loader and a vial coupler device. The transporter/loader device serves as a container in which to transport a quantity of medication and as a loading device for loading a selected dosage into the injector device, while the vial coupler device serves to couple the transporter/loader device to the vial. Alternately, the dose dispenser may take the form of a single vial adapter device. In either case, once the dose dispenser is attached to the vial, there is no exposed needle to worry about.

In the case of the vial coupler, for example, the user attaches the vial coupler to the vial by piercing the self-sealing lid with a needle on the vial coupler. The vial coupler includes a connector arrangement for needleless coupling to the transporter/loader device so that when it is desired to withdraw a quantity of medication from the vial, the user screws the transporter/loader device onto the vial coupler without having to manipulate a needle, transfers one or more provide a very functional, convenient to use, and safe system for the self-administration of medication.

Generally, a needleless injection device constructed according to the invention includes a unit that is dimensioned and arranged to be grasped in the hand of a user. It includes a barrel portion, a gas storage portion, and an intermediate portion that extends between the two.

According to a major aspect of the invention, this unit is integrally formed to carry its own power source. In other words, it is a single-shot unit that can be conveniently loaded with a selected dosage through an aperture in the discharge end of the barrel portion, be used, and then be discarded. This disposable arrangement greatly simplifies the structure and mechanism employed.

According to another aspect, a compressed gas acts upon a piston face that is larger than a plunger face that acts upon the selected dosage. This increases the pressure applied to the selected dosage in order to increase the pressure with which it is ejected from the barrel portion.

Yet another aspect of the invention features a breakable member such as a glass quill that extends through the gas storage portion, from a storage compartment to an expansion chamber. The breakable can be broken in order to release the gas into the expansion chamber and a trigger mechanism is provided for doing this. Thus, the injector device can be fired without first having to cock it.

The above mentioned and other objects and features of this invention and the manner of attaining them will become apparent, and the invention itself will be best understood, by reference to the following description taken in conjunction with the accompanying illustrative drawings.

BRIEF DESCRIPTION OF THE DRAWINGS

FIG. 2 is an enlarged cross sectional view of the injector device taken on line 2—2 of FIG. 1 with the device loaded and ready for firing, but with the safety on;

DESCRIPTION OF THE PREFERRED EMBODIMENTS

Referring now to the drawings, there is shown an injector device 20 (FIGS. 1-4), a vial coupler device 21 and a transporter/loader device 22 that combine to function as a dose dispenser (FIGS. 5-8 and FIGS. 9-13), and a vial adapter device 23 that functions as another form of dose dispenser (FIGS. 14-17).

These components facilitate the self-administration of medication, especially the administration of medications such as insulin that may involve frequent injections of precise dosages, and they are discussed according to the following outline:
  I. Injector Device
  II. Vial Coupler Device
  III. Transporter/Loader Device
  IV. Vial Adapter Device

I. Injector Device

Figure 1:
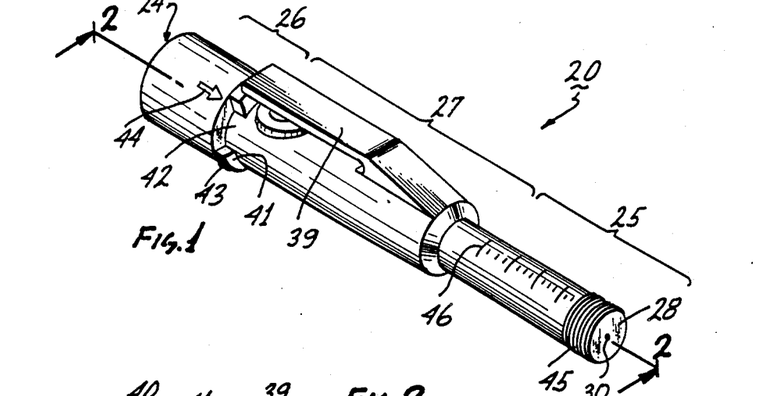
FIG. 1 of the drawings is a perspective view of a needleless injector device constructed according to the invention.

Generally, the device 20 includes an integral unit 24 that is dimensioned and arranged to be grasped in the hand of a user. It is integral in the sense that it carries its own one-shot power source instead of being reloadable and reuseable. As an idea of size, the unit 24 may be about ten or eleven centimeters long and about one and one-half centimeters across at its widest point. Of course, these dimensions are not critical.

Preferably composed of an injected molded thermoplastic material, the unit 24 includes a barrel portion 25, a gas storage portion 26, and an intermediate portion 27. The barrel portion extends from the intermediate portion 27 to a discharge end 28 of the barrel portion 25 and it defines a bore 29 (FIGS. 2-4) that extends from the intermediate portion 27 to an orifice or aperture 30 in the discharge end 28.

The gas storage portion 26 defines a gas storage compartment 31 in which is disposed a compressed gas such as $CO_2$. This may be introduced during manufacture by suitable means, such as through an opening that is then sealed with a plug, and the compressed gas is used as an energy source for injecting the selected dosage from the bore 29 through the aperture 30. In other words, it released from the storage compartment 31 to propel the selected dosage out of the barrel portion 29.

The intermediate portion 27 defines an expansion chamber or chamber 32 that is used for this purpose. Preferably, the chamber 32 is cylindrically shaped. The intermediate portion 27 and the chamber 32 extend between the gas storage portion 26 and the barrel portion 25, and a piston 33 combines with a pushrod 34 to couple force from compressed gas entering the chamber 32 to a plunger 35 disposed within the bore 29, the piston 26 having a size and shape conforming to the cross sectional size and shape of the chamber 32.

The invention includes gas release means for releasing the compressed gas from the compartment 31 so that the compressed gas can flow into the chamber 32. This is accomplished in the illustrated device 20 with a breakable member in the form of a hollow glass quill 36 that extends through the gas storage portion 26 as shown (FIG. 2), from an open end 37 in the storage compartment 31 a closed end 38 in the chamber 32. It may be suitably bonded in this position.

The gas release means so formed is actuated by breaking off the closed end 38 or the glass quill 36. The invention includes trigger means for enabling a user to actuate the gas release means, and this is accomplished in the device 20 with a trigger mechanism that includes a trigger 39 attached to the intermediate portion 27 for movement when depressed by the user. When depressed, a firing pin 40 presses against add breaks the fragile glass quill to release the compressed gas into the chamber 32. The gas flows from the storage compartment 31 through the hollow interior of the glass quill 36.

But in order to operate the trigger the user must first position a safety ring 41 (FIG. 1) in an off position. The safety ring 41 circumscribes the intermediate portion 27 as shown in FIG. 1, and it is mounted for rotational movement so that a space 42 in the safety ring 41 can be moved into alignment with the trigger 39. This is the off position in which the trigger 39 can be depressed to fire the device 20, and it is indicated by alignment of a ridge 43 on the safety ring 41 with an indicator 44 provided for this purpose. The ridge also enhances user engagement of the safety ring 41.

Unless the safety ring 41 is in the off position, the trigger 39 is blocked from being depressed. The safety ring 41 is shown blocking the trigger 39 in FIGS. 1 and 2, and in the off position in FIGS. 3 and 4.

Operationally, the user grasps the device 20 and removes any sterility cover that might be provided over the discharge end 28, such as a cap member (not shown) that is arranged to be screwed onto a threaded end portion 45 of the barrel portion 25, for example. The threaded end portion 45 may employ a two-start thread that mates with threaded portions on the transporter/loader and vial adapter dose dispenser devices subsequently described.

Figure 4:
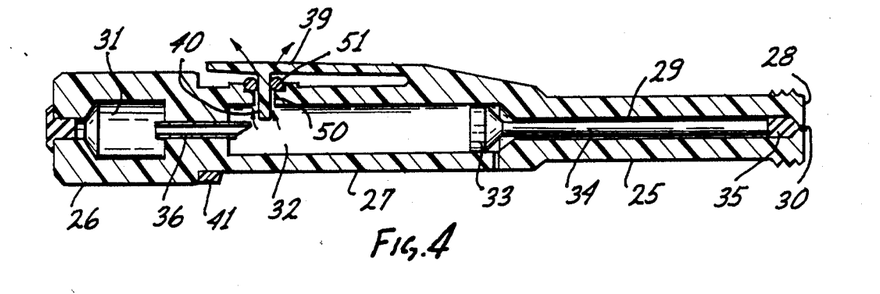
FIG. 4 is another cross sectional view similar to FIG. 2 showing the injector device with the dosage fully injected, the trigger released, and the compressed gas discharging.
Figure 5:
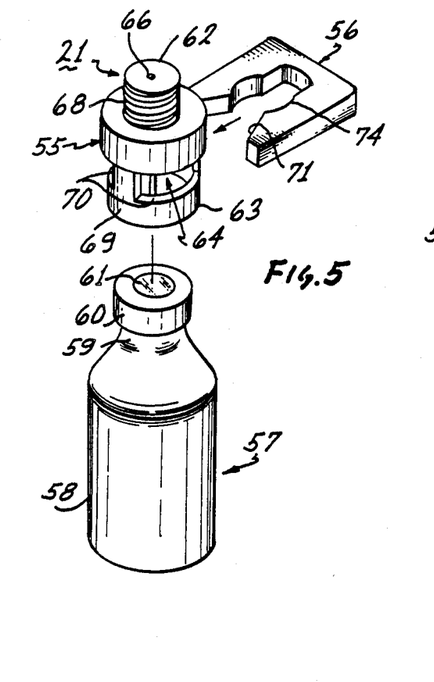
FIG. 5 a perspective view of a vial coupler device constructed according to the invention showing the manner in which it mounts on a vial.
Figure 6:
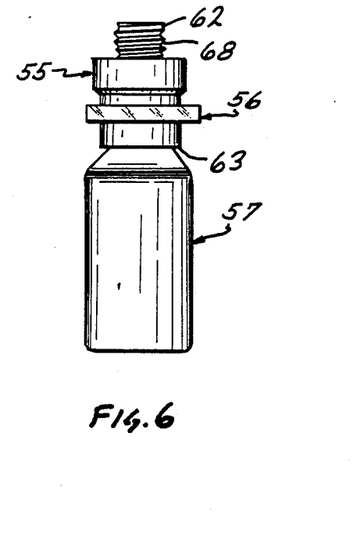
FIG. 6 is an elevation view of the vial coupler device fully mounted on the vial.
Figure 7:
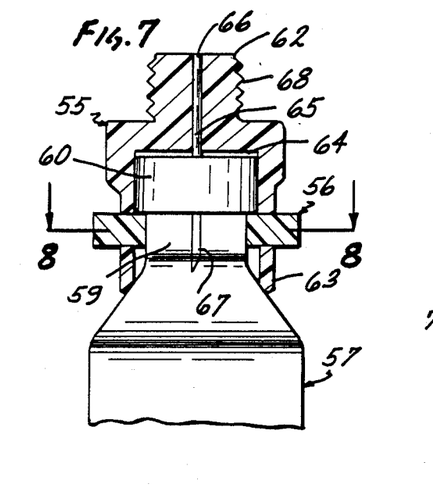
FIG. 7 is an enlarged elevation view of the vial coupler and a portion of the vial with portions shown in cross section.
Figure 8:
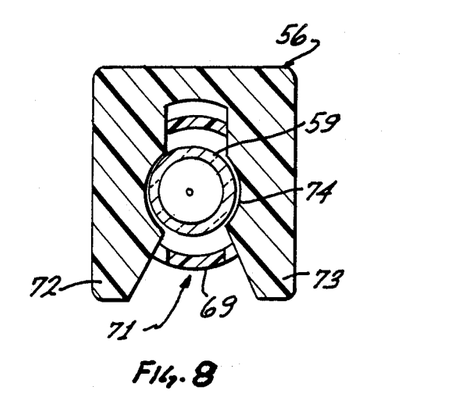
FIG. 8 is a cross sectional view taken on line 8—8 of FIG. 7.

At this point in the operation, the plunger 35 is disposed fully forward in the bore 29 in the position shown in FIG. 4. Using suitable dose dispenser means, such as one of the dose dispensers devices subsequently described, the user loads a selected dosage of medication through the aperture 30 into the bore 29. This may be done with by attachment to the threaded end portion 45 of the barrel portion 25 (FIG. 1).

Figure 2:
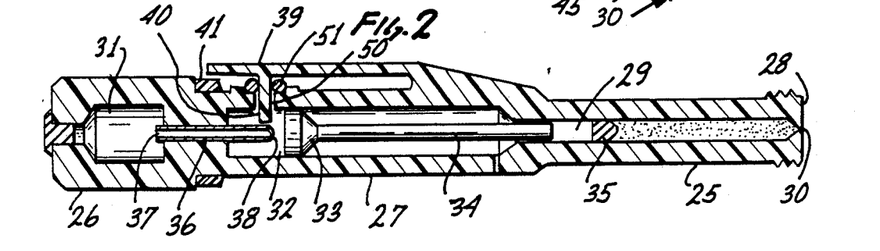

As the selected dosage is loaded into the bore 29, it forces the plunger 35 away from the discharge end 28 to a position such as that shown in FIG. 2. Preferably, at least a portion of the barrel portion 25 is sufficiently transparent to enable a user to visually discern the position of the plunger 35 relative to a plurality of graduations 46 provided on the barrel portion 25. This enables the user to ascertain precisely how much medication has been loaded into the bore 29 so that the loading procedure can be stopped as soon as the selected dosage has been loaded.

FIG. 2 shows a position the plunger 35 might occupied when loading has been completed, the stippling between the plunger 35 and the aperture 30 representing the selected dosage of medication that has been loaded into the bore 29.

At this point in the self-administration of the medication, the user turns the safety ring 41 to the off position. Next, the user places the discharge end 28 proximate the user's skin at a point where the medication is to be injected and depresses the trigger 39 to fire the device 20.

Figure 3:
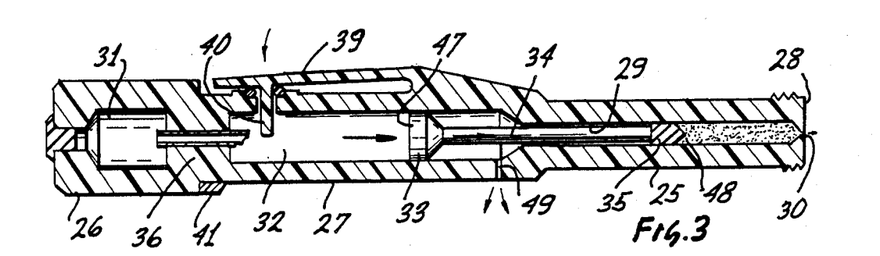
FIG. 3 is another cross sectional view similar to FIG. 2 showing the injector device after firing with the safety off, the trigger depressed, and the dosage partially injected.

This results in the firing pin 40 breaking the glass quill 36 so that the compressed gas rushes through the quill 36 into the chamber 32 as shown in FIG. 3. In this regard, little transverse pressure is required to break the glass quill 36 so that a few ounces of pressure may be all that is needed to depress the trigger 39 sufficiently to fire the device 20.

As the compressed gas rushes into the chamber 32, it acts against a piston face 47 of the piston 33 (FIG. 3) and this drives the piston toward the bore 29 with the result that the pushrod 34 contacts the plunger 35 and drives it toward the aperture 30. This action causes a plunger face 48 of the plunger 35 to act against the medication and force it out of the aperture 30 in a high pressure jet depicted by the arrow extending outwardly from the aperture 30 in FIG. 3.

The plunger 35 may be composed of a rubber material, for example, and be configured conform to the bore cross section. Thus, medication does not flow past the plunger 35 toward the piston 33. In addition, the plunger face 48 is configured as shown to conform to the shape of the bore 29 at the aperture 30 so that no medication remains in the bore 29 after firing.

According to one aspect of the invention, the piston face 47 has a larger surface area than the plunger face 48. This surface area differential results in more pressure being applied to the medication than the compressed gas applies to the piston face 47. This pressure amplification may be utilized to achieve an injection pressure at the aperture 30 of about 2,500–5,000 psi, for example, depending on the precise configuration employed, whereas the compressed gas might exhibit a pressure of about 840 psi at room temperature.

As the piston 33 moves toward the discharge end 30, gas ahead of the piston 33 (between the piston 33 and the barrel portion 25) vents through an opening 49 provided for this purpose (FIG. 3). Thus, the opening 49 serves as vent means disposed intermediate the piston 33 and the plunger 35 for enabling gas to escape from a region ahead of the piston 33.

After firing, the compressed gas discharges through a discharge port 50 provided around the firing pin 40 (FIG. 4). This may be a hole through which the firing pin 40 extends. However, the discharge port 50 is sealed momentarily when the user operates the trigger 39. This delays the escape of the compressed gas from the chamber 32 until the piston 33 has been driven substantially all the way to the fully fired position shown in FIG. 4.

The delay is accomplished by utilizing an O-ring seal 51 disposed in the position shown in FIGS. 2 and 4 so that when the trigger 39 is depressed, the trigger 39 presses against the seal 51 to seal the discharge port 50. The seal 51 may be composed of a know medical grade elastomeric material for this purposes. When the trigger 39 is released, it disengages the seal 51 to open or unseal the discharged port 50 so that the compressed gas can escape.

Other means may be used for delaying the escape of compressed gas through the discharge port 50. For example, a tapered firing pin may be provided along with a discharge port having a mating taper so that the firing pin wedges into the discharge port momentarily during firing.

II. Vial Coupler Device

The vial coupler device 21 is so named to reflect the function it performs. It provides needleless coupling of the transporter/loader device 22 that is subsequently described to a conventional vial, such as a vial 57 in FIGS. 5–8, so that the user does not have to manipulate a needle through a self-sealing lid of the vial 57 each time it is desired to withdraw a quantity of medication from the vial 57.

In other words, the vial coupler device 21 includes a needle for piercing the self-sealing lid, but coupling to the transporter/loader device 22 is without a needle. Thus, the user does not have to manipulate a needle frequently, nor be exposed to a needle.

Generally, the vial coupler device 21 includes a coupler member 55 and a collar member 56 arranged to lock the coupler member 55 on the vial 57. In this regard, the vial 57 has an enlarged lower portion 58, a narrower neck portion 59, and a lid portion 60 that is slightly enlarged in comparison to the neck portion 59. The lid portion 60 is covered with a self-sealing lid 61. The lid 61 is self-sealing in the conventional sense that it can be pierced by a cannula such as a hypodermic needle, and when the needle is removed, the resulting hole in the lid 61 closes by itself.

As an idea of size, the vial 57 may be a conventional ten milliliter medication bottle containing insulin. The bottle may be about five centimeters high, for example, with the lower portion 58 about two and one-half centimeters in diameter, the neck portion 59 about one centimeter in diameter, and the lid portion 60 about one and one-half centimeters in diameter, these dimensions being commonly used by vial manufacturers. Of course, these dimensions are approximate and critical only to the extent that the vial coupler device must be dimensioned accordingly.

The coupler member 55 extends from a closed end 62 to an open end 63, and it defines a hollow interior 64 that is dimensioned and arranged to receive the lid portion 60 of the vial 57 when the open end 63 is placed over the lid portion 60 of the vial 57. As this is done, a cannula 65 pierces the self-sealing lid 61.

Something like a hypodermic needle, the cannula 65 has a first end portion 66 attached to the closed end portion 62 of the coupler member 55 and a second end portion 67 disposed toward open end 63. The cannula 65 is dimensioned and arranged to pierce the self-sealing lid 61 and provide a passage through which to convey medication to the first end portion 66 of the cannula 65. In this connection, the second end portion 67 is slightly recessed from the open end 63 to inhibit contact by and resultant injury to the user.

A threaded end portion 68 is provided on the coupler member 55 for use in coupling the cannula 65 to other components. For this purpose, it is suitably dimensioned and so that it can be attached to the transporter/loader device subsequently described. Thus, the threaded end portion 68 serves as means for enabling the transporter/loader device to be attached the coupler member 55 over the closed end 62 so that the transporter/loader device is in fluid communication with the cannula 65.

According to another aspect of the invention, the locking collar 56 locks the coupler member 55 onto the vial 57. Preferably, this is done to inhibit removal and reuse of the coupler member 55. In other words, the coupler member 55 must be discarded with the vial 57 to prevent the contamination that might accompany reuse. This may be important in order to comply with applicable governmental regulations.

Like the coupler member 55, the collar member 56 may be composed of an injection molded thermoplastic material, and it functions to lock the coupler member 55 on the vial 57 by snapping onto the neck portion 59. For this purpose, the coupler member 55 includes a slotted portion 69 that defines two radially opposite slots 70 (FIG. 5) through which the collar member 56 is placed.

The slotted portion 69 is disposed between the closed end 62 and the open end 63 in a position such that the slots 70 align with the neck portion 59 of the vial 57. The collar member 56 defines an open ended channel 71 that is dimensioned and arranged to receive the neck portion 59 when the collar member 56 is inserted through the slots 70.

Resiliently deformable opposite side portions 72 and 73 of the collar member 56 (FIG. 8) spread apart slightly as the neck portion 59 is forced into the channel 71. Then, they recover to retain the neck portion 59 at an enlarged central portion 74 of the channel 71.

Thus, the vial coupler device 21 can be attached to the vial 57 by placing the coupler member 55 over the lid portion 60 and inserting the locking collar member 56 through the slots 70 to engage the neck portion 59 of the vial 57. When this is done, the cannula 65 pierces the self-sealing lid 61 to establish fluid communications between the first end 66 of the cannula 55 and the interior of the vial 57.

III. Transporter/Loader Device

The transporter/loader device 22 is so named to reflect the dual function it serves. It serves as a transportable container in which to carry medication apart from the vial 57 and as a loading device for needleless loading of the selected dosage into the injector device 20.

Figures 9, 10, 11, 12, 13:
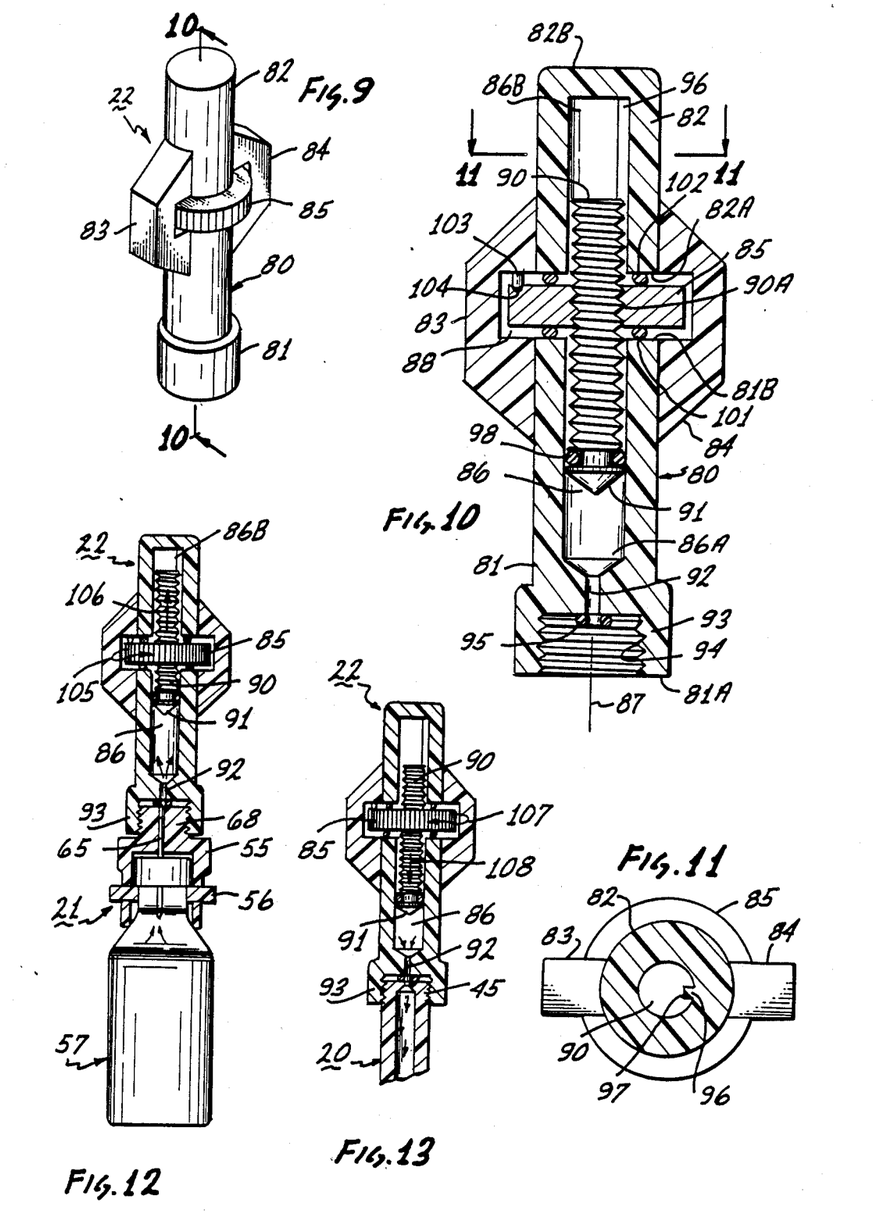
FIG. 9 is perspective view of a transporter/loader device constructed according to the invention.
FIG. 10 is an enlarged cross sectional view taken on line 10—10 of FIG. 9.
FIG. 11 is an enlarged cross sectional view of the transporter/loader device taken on line 13—13 of FIG. 11 showing antirotation aspects.
FIG. 12 is an elevation view with portions in cross section showing operation of the transporter/loader device with the vial coupler device in withdrawing the quantity of medication from the vial.
FIG. 13 is another elevation view with portions in cross section showing operation of the transporter/loader device in loading the selected dosage the injector device.

Generally, the transporter/loader device 22 includes an elongated member 80 having attached forward and rearward portions 81 and 82 that are attached together with bridge members 83 and 84 to provide a space in which a thumbwheel 85 is disposed (FIG. 9).

The forward portion 81 extends between forward and rearward ends 81A and 81B of the forward portion 81 and the rearward portion 82 extends forward and rearward ends 82A and 82B of the rearward portion 82 (FIG. 10).

The body member 80 defines a bore 86 extending along a bore axis 87 from a forward end portion 86A of the bore 86 that is disposed toward the forward end 81A of the forward portion 81, to a rearward end portion 86B of the bore 86 that is disposed toward the rearward end 82B of the rearward portion 82.

The device 22 includes means for attaching the forward and rearward portions 81 and 82 together so that there is a space 88 between the rearward end 81B of the forward portion 81 and the forward end 82A of the rearward portion 82 (FIG. 10). The bridge members 83 and 84 serve this function, and they may be attached together with the forward and rearward portions 81 and 82 in an integral unit composed of an injection molded thermoplastic material.

The thumbwheel 85 may also be composed of an injection molded thermoplastic material, and it is disposed in the space 88 between the forward and rearward portions 81 and 82 where it functions as a component that the user can turn in order to move a threaded shaft or plunger 90 disposed within the bore 86 (FIG. 10).

The plunger 90 is may be composed of a thermoplastic material and it extends through a threaded hole 90A in the thumbwheel 85 to a plunger face 91 (FIG. 10). The forward portion 86A of the bore 86 narrows to a passage 92, and the plunger face 91 conforms to the shape of this forward portion.

The passage 92 extends to a threaded end portion or connector portion 93 having an interior thread 94 that mates with the threaded portion 68 of the vial adapter device 21 and the threaded portion 45 of the injector device 20. This arrangement provides means for attaching the forward portion 81 of the elongated member 80 first to the vial coupler device 21 and then to the injector device 20, while a medical grade elastomeric O-ring seal 95 provides sealing engagement with the devices 20 and 21 when the device 22 is screwed on to them.

Attachment to the vial coupler device 21 places the bore 86 in the elongated member 80 in fluid communication with the cannula 67 to enable withdrawal of the quantity of medication. Attachment to the injector device 20 places the bore 86 in the elongated member 80 in fluid communication with the bore 29 in the barrel portion 25 to enable loading of the ejector device 20.

A rail 96 (FIGS. 10 and 11) extending along at least a portion of one of the forward and rearward portions 81 and 82 (in this case the rearward portion 82) mates with a channel 97 in the plunger 90 (FIG. 11) to serve as means for preventing rotation of the plunger 90 with the thumbwheel 85. Of course, other suitable antirotation means may be employed, such as a plunger having one or more longitudinally extending flat surfaces that mate with the shape of a non-circular bore.

A medical grade elastomeric O-ring seal 98 circumscribes the plunger 90 near the plunger face 91. It provides a seal between the plunger 90 and the forward portion 81 that inhibits passage of medication past the plunger face 91 toward the rearward portion 86B of the bore 86.

Similar medical grade O-ring seals 101 and 102 between the thumbwheel 85 and the forward and rearward portions 81 and 82 (FIG. 10) provide sealing engagement that inhibits passage of contaminants into the bore 86. They function as sealing means for maintaining a seal between the thumbwheel 85 and each of the forward and rearward portions 81 and 82. The seal 101 circumscribes the plunger 90 between the thumbwheel 85 and the rearward end 81B of the forward portion 81 for this purpose, and the seal 102 circumscribes the plunger 90 between the thumbwheel 85 and the forward end 82A of the rearward portion 82.

According to one aspect of the invention, the device 22 includes turns counting means for producing a human sensible signal as the thumbwheel member 85 is rotated for purposes of enabling a visually impaired user to determine the amount of medication being dispensed. This is accomplished in the illustrated device 22 with a protruding member 103 on the elongated member 80 that extends into indentations at spaced apart locations around the periphery of the thumbwheel 85, such as the indentation 104 in FIG. 10.

Four equally spaced-apart indentations 104 on the thumbwheel 85 result in an audible sound being produced each ninety degrees as the thumbwheel 85 is rotated. A slight vibration that can be discerned by the sense of touch is also thereby produced. Thus, the user can count the occurrences of these sounds or vibrations to keep track of the amount of medication dispensed.

To further this purpose, the bore 86 in the elongated member 80 and the plunger 90 are dimensioned and arranged to enable a user to dispense 0.01 milliliter of medication from the bore 86 when the thumbwheel 85 is turned ninety degrees. This is the volume of one unit of insulin.

Operationally, the vial coupler device 21 is attached to the vial 27, and then the connector portion 93 of the device 22 is screwed onto the threaded portion 68 of the vial coupler device 21 as illustrated in FIG. 12. This i done with the plunger 90 positioned so that the plunger face 91 is fully advanced toward the passage 92. In other words, there is substantially no space between the plunger face 91 and the passage 92 so that the device 22 is substantially empty.

Then, the user rotates the thumbwheel 85 to move the plunger 90 toward the rearward end portion 86B of the bore 86. This produces a pressure differential or suction that withdraws medication from the vial 57 through the cannula 67 of the vial adapter device 21 into the bore 86 of the transporter/loader device 22.

As this is done, it is possible for a visually impaired user to count the number of quarter turns of the thumbwheel 85 until the desired quantity of medication is withdrawn from the vial 57 into the device 22.

Preferably, the plunger 90 includes a left hand thread. Thus, rotating the thumbwheel 85 in a counterclockwise direction as indicated by an arrow 105 in FIG. 12 results in the plunger 90 moving toward the rearward end portion 86B of the bore 86 as indicated by an arrow 106. In addition, medication may be withdrawn from the vial 57 by raising the vial 57 relative to the device 22 instead of retaining the vial 57 lowered in the position that is shown in FIG. 12 for illustrative convenience.

With the desired quantity of medication withdrawn from the vial 57, disposed in the bore 86 between the plunger face 91 and the passage 92, the device 22 is detached or unscrewed from the vial coupler device 21 and transporter by the user until it is time for an injection. Then, the user grasps the injector device 20, removes any sterility cover, and screws the connector portion 93 of the transporter/loader device 22 onto the threaded portion 45 of the injector device 20 as illustrated in FIG. 13.

With the transporter/loader device 22 screwed onto the injector device 20, the user rotates the thumbwheel 85 clockwise as indicated by an arrow 107 in FIG. 13. This results in the plunger 90 moving toward the injector device 20 as indicated by an arrow 108. The plunger face 91 forces the selected dosage through the passage 92 into injector device 20, while the visually impaired user may, at this point, count the turns of the thumbwheel 85 until the selected dosage is loaded into the injector device 20.

Next, the user verifies that the correct dosage is within the injector device 20 by viewing the plunger 35 in the injector device 20 relative to the graduations 46 on the barrel portion 25 as discussed previously with reference to FIGS. 1-4. Then, the user unscrews the transporter/loader device 22 from the injector device 20 and stores the transporter/loader device 22 for later reuse (the bore 86 may hold up to three doses of insulin, for example). The injector device 20 is then operated to injected the selected dosage, and then the device 20 is discarded.

IV. Vial Adapter Device

The vial adapter device 23 combines features of the vial coupler device 21 with features of the transporter/loader device 22 in a single unit and it is so named to reflect the function it performs. It directly interfaces the injector device 20 to the vial 57.

This means that the vial adapter device 23 includes a needle for piercing the self-sealing lid of the vial 57. With the illustrated injector device 20, this also means that the threaded portion 45 of the injector device 20 can be connected to the vial adapter device 23, thereby providing needleless coupling to the injector device 20.

With the vial adapter device 23 simultaneously attached in this way to both the injector device 20 and the vial 57, a valve arrangement is operated to switch between them in order to enable use as a dose dispenser for loading the injector device 20 directly from the vial 57.

As already discussed, the vial coupler device 21 and the transporter/loader device 22 combine to serve as a dose dispenser also. From the above descriptions of the devices 21 and 22, the structure and operation of the vial adapter device 23 becomes more apparent.

Generally, the vial adapter device 23 includes a vial adapter body member 120 that is similar in some respects to the elongated member 80 of the device 22. It includes attached forward and rearward portions 121 and 122 that are attached together with bridge members 123 and 124 to provide a space in which a thumbwheel 125 is disposed (FIG. 14).

Figures 14, 15, 16, 17:
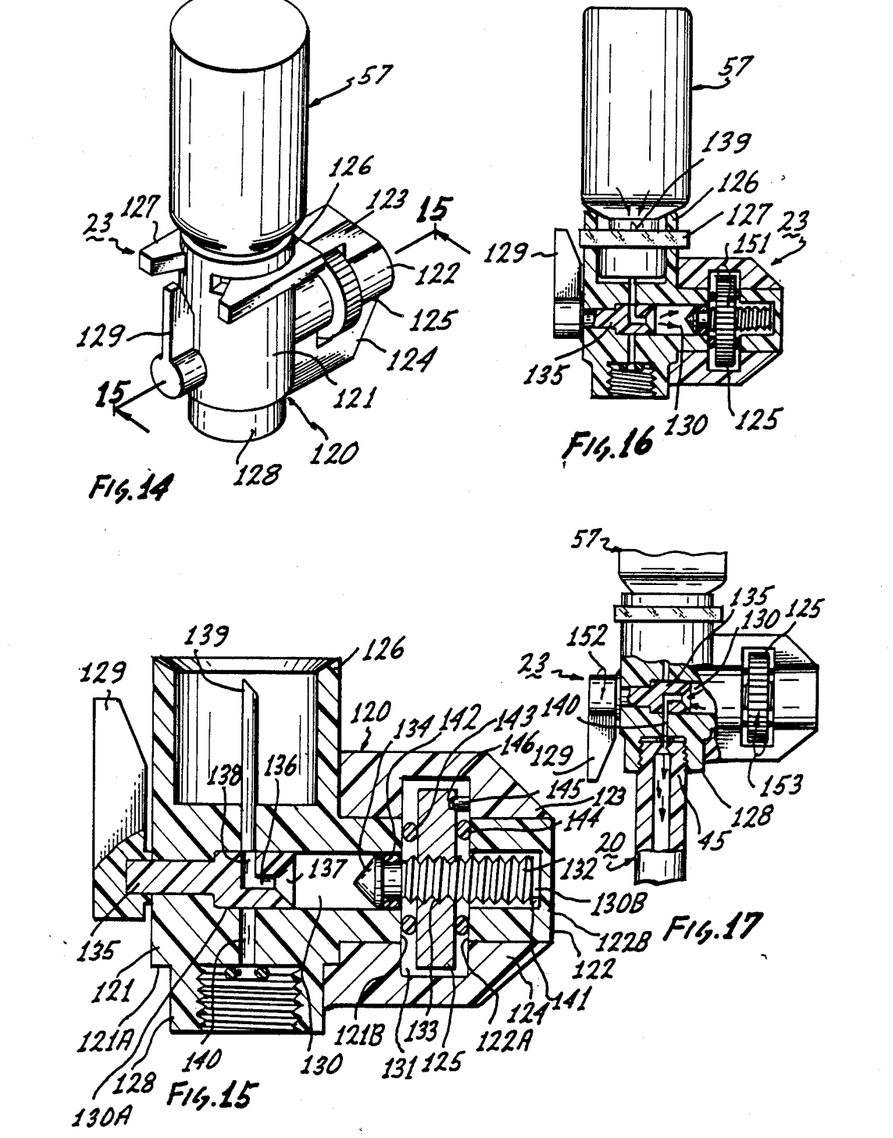
FIG. 14 is a perspective view of a vial adapter device constructed according to the invention shown attached to the vial.
FIG. 15 is an enlarged cross sectional view taken on line 15—15 of FIG. 14.
FIG. 16 is an elevation view with portions in cross section showing operation of the vial adapter device in withdrawing the quantity of medication from the vial.
FIG. 17 is another elevation view with portions in cross section showing operation of the vial adapter device in loading the selected dosage into the injector device.

The forward portion 121 includes a vial coupler portion 126 and a coupler collar 127 for attaching the forward portion 121 to the vial 57 (FIG. 14). These are similar in many respects to the coupler member 55 and collar member 56 of the vial coupler device 21 (FIG. 5) so that they are not described in detail.

The forward portion 121 also includes an injector connector portion 128 (FIG. 14) for attaching the forward portion 121 to the threaded portion 45 of the injector device 20 (FIG. 1), and this is similar in many respects to the connector portion 93 of the transporter/loader device 22 (FIG. 10) so that it is not described in detail.

An actuator member or knob 129 (FIG. 14) operates a valve arrangement subsequently discussed to switch the vial adapter device 23 between the two. With the vial coupler portion 126 attached to the vial 57 and the injector connector portion 128 attached to the threaded portion 45 of the injector device 20, the user operates the knob 129 to a first knob position as illustrated in FIG. 14. In this regard, the knob may be shaped as illustrated to indicate the position it is in. With the knob in the first position, the user withdraws the quantity of medication from the vial 57 into the vial adapter body member 120, moves the knob 129 one hundred eighty degrees to a second valve position, and loads the selected dosage into the injector device 20.

Further structural details are shown in FIG. 15. The forward portion 121 extends between forward and rearward ends 121A and 121B of the forward portion 121 and the rearward portion 122 extends forward and rearward ends 122A and 122B of the rearward portion 122.

The body member 120 defines a bore 130 that is similar but shorter than the bore 86 of the device 22. It may be only large enough to hold slightly more than one unit of insulin, for example. The bore 130 extends from a forward end portion 130A of the bore 130 that is disposed toward the forward end 121A of the forward portion 121, to a rearward end portion 130B of the bore 130 that is disposed toward the rearward end 122B of the rearward portion 122.

The device 23 includes means for attaching the forward and rearward portions 121 and 122 together so that there is a space 131 between the rearward end 121B of the forward portion 121 and the forward end 122A of the rearward portion 122. The bridge members 123 and 124 serve this function. Similar to the bridge members 83 and 84 of the device 22 (FIGS. 9-13), the bridge member 123 and 124 may be attached together with the forward and rearward portions 121 and 122 in an integral unit composed of an injection molded thermoplastic material.

The thumbwheel 125 may also be composed of an injection molded thermoplastic material, and it is disposed in the space 131 between the forward and rearward portions 121 and 122 where it functions as a component that the user can turn in order to move a threaded shaft or plunger 132 disposed within the bore 130 (FIG. 15).

The plunger 132 is may be composed of a thermoplastic material and it extends through a threaded hole 133 in the thumbwheel 125 to a plunger face 134 that faces a valve element 135 disposed within the forward portion 130A of the bore 130. The valve element 135 conforms to the shape of the bore 130 and is attached to the knob 129 so that movement of the knob 129 rotates the valve element 135 within the bore 130.

The valve element 135 defines a passage 136 extending between first and second ends 137 and 138 of the passage 136. The first end 137 faces axially toward the plunger face 134 and the second end 138 faces radially, the shape of the plunger face 134 conforming to the first end 137.

When the knob 129 is turned to the first knob position, the valve element 135 rotates to the first valve position in which the second end 138 of the passage 136 faces a cannula 139 that functions as a first port for providing fluid communications with the vial 57. In the first valve position, the second end 138 faces the first port so that the cannula 139 and the bore 130 are in fluid communications. This is the state shown in FIG. 15.

When the knob 129 is turned to the second knob position, the valve element 135 rotates to a second valve position in which the second end 138 faces a passage 140 that functions as a second port for providing fluid communications with the injector device 20. In the second valve position, the second end 138 faces the second port so that passage 140 and the bore 130 are in fluid communications.

The cannula 139 is similar to the cannula 67 of the device 21 to enable it to pierce the self-sealing lid of the vial 57 and provide a passage through which to withdrawn the quantity of medication into from the vial 57 into the bore 130. The passage 140 is similar to the passage 92 of the device 22, and the injector connector portion 128 may have suitable means such as an O-ring seal to facilitate coupling to the threaded portion 45 of the injector device 20, similar to the O-ring seal 95 of the device 22.

In addition, the vial adapter device 23 includes a rail 141 extending along at least a portion of one of the forward and rearward portions 121 and 122 (in this case the rearward portion 122) that mates with a channel in the plunger 132 that is similar to the channel 97 in the plunger 90 of the device 22. This arrangement serves as means for preventing rotation of the plunger 132 with the thumbwheel 125 like the antirotation means of the device 22.

A medical grade elastomeric O-ring seal 142 circumscribes the plunger 132 near the plunger face 134. It provides a seal between the plunger 132 and the forward portion 121 that inhibits passage of medication past the plunger face 134 toward the rearward portion 130B of the bore 130.

Similar medical grade O-ring seals 143 and 144 between the thumbwheel 125 and the forward and rearward portions 121 and 122 provide sealing engagement that inhibits passage of contaminants into the bore 130.

They function as sealing means for maintaining a seal between the thumbwheel 125 and each of the forward and rearward portions 121 and 122. The seal 143 circumscribes the plunger 132 between the thumbwheel 125 and the rearward end 121B of the forward portion 121 for this purpose, and the seal 144 circumscribes the plunger 132 between the thumbwheel 125 and the forward end 122A of the rearward portion 122.

According to one aspect of the invention, the device 23 includes turns counting means for producing a human sensible signal as the thumbwheel member 125 is rotated for purposes of enabling a user to determine the amount of medication being dispensed. This is accomplished in the illustrated device 23 with a protruding member 145 on the body member 120 that extends into indentations at spaced apart locations around the periphery of the thumbwheel 125, such as the indentation 146 in FIG. 15.

Four equally spaced-apart indentations 146 on the thumbwheel 125 result in an audible sound being produced each ninety degrees as the thumbwheel 125 is rotated. A slight vibration that can be discerned by the sense of touch is also thereby produced. Thus, much like operation of the transporter/loader device 22, the user can count the occurrences of these sounds or vibrations to keep track of the amount of medication dispensed.

Also like the device 22, the bore 130 in the body member 120 and the plunger 132 are dimensioned and arranged to enable a user to dispense 0.01 milliliter of medication from the bore 130 when the thumbwheel 125 is turned degrees, this volume representing one unit of insulin. As previously described, this combines with the turns counting means to assist a visually impaired user.

Operationally, the vial coupler portion 126 of the vial adapter device 23 is placed atop the vial 57 and secured with the coupler collar 126, much like the way the vial coupler device 21 is attached. This places the cannula 139 in fluid communication with the vial 57 so that the quantity of medication can be withdrawn. Preferably, the device 23 is left mounted this way and discarded with the vial 57 when the vial is empty.

In order to withdraw the quantity of medication into the vial adapter device 23, the plunger 132 is first positioned so that there is substantially no space between the plunger face 134 and the valve element 135. Then, with the vial 57 raised in relationship to the vial adapter device 23 and the knob 129 in the first knob position as shown in FIG. 16, the user rotates the thumbwheel 125 counterclockwise as indicated by an arrow 151 in FIG. 16. With the valve element 135 in the first valve position, the bore 130 is in fluid communication with the cannula 139 and thereby with the vial 57 so that operation of the thumbwheel 125 in the direction of the arrow 151 withdraws the quantity of medication from the vial 57 through the cannula 139 into the bore 130.

In order to load the selected dosage into the injector device 20, the user attaches the injector connector portion 128 to the threaded portion 45 of the device 20 as shown in FIG. 17. Then, the user rotates the knob 129 as indicated by an arrow 152 to the second knob position. This rotates the valve element 135 to the second valve position so that the second end 138 of the passage 136 is aligned with the passage 140. This in turn places the bore 130 of the vial adapter device 23 in fluid communication with the passage 136 and thereby with the injector device 20.

Then the user rotates the thumbwheel 125 in a clockwise direction as indicated by an arrow 153 in FIG. 17. This forces the selected dosage out of the bore 130 and through the passages 136 and 140 into the injector device 20. The user views the relationship of the plunger 35 to the graduations 46 to verify the dosage, or, in the case of a visually impaired user, the user may count the turns of the thumbwheel 125 as described in connection with operation of the transporter/loader device 22. Then the user detaches the vial adapter device 23 from the injector device 20 and utilizes the injector device 20 as described above.

Thus, the invention provides a needleless injector system that greatly facilitates the self-administration of medication. The injector is a lightweight, portable, disposable, and self-contained device that combines with the vial coupler and the transporter (or the single unit vial adapter) to do this in a very functional, convenient to use, and safe system.

Although an exemplary embodiment of the invention has been shown and described, many changes, modifications, and substitutions may be made by one having ordinary skill in the art without necessarily departing from the spirit and scope of the invention.

What is claimed is:

1. A method of administering a medication, comprising:
   providing at least one needleless injector device having a barrel portion, a gas storage portion, and an intermediate portion extending between the barrel portion and the gas storage portion;
   providing dose dispenser means for needleless loading of the injector device with medication withdrawn from a vial having a self-sealing lid;
   attaching the dose dispenser means to the vial;
   withdrawing a quantity of medication from the vial into the dose dispenser means;
   coupling the dose dispenser means to the injector device;
   loading a selected dosage from the dose dispenser means into the barrel portion of the injector device through an aperture in the barrel portion;
   detaching the dose dispenser means from the injector device; and
   operating the loaded injector device to eject the selected dosage from the injector device and thereby pass the selected dosage through the skin.

2. A method as recited in claim 1, wherein the step of providing dose dispenser means includes:
   providing dose dispenser means that includes transporter/loader means for transporting and loading the medication and vial coupler means for needleless coupling of the transporter/loader means to the vial for purposes of withdrawing a quantity of medication from the vial into the transporter/loader means.

3. A method as recited in claim 2, wherein the step of withdrawing the medication includes:
   attaching the vial coupler means to the vial;
   attaching the transporter/loader means to the vial coupler means; and
   operating the transporter/loader means to withdraw the quantity of medication from the vial.

4. A method as recited in claim 3, wherein the step of loading the selected dosage into the injector device includes:
   attaching the transporter/loader means to the injector device; and operating the transporter/loader means to load the selected dosage into the injector device.

5. A method as recited in claim 1, wherein the step of providing dose dispenser means includes:

providing dose dispenser means in the form of vial adapter means that includes injector attachment means for needleless coupling of the vial adapter means to the injector device, vial attachment means for coupling the vial adapter means to the vial, and a valve arrangement that is adjustable between a first valve position enabling withdrawal of the quantity of the medication from the vial into the vial adapter means and a second valve position enabling loading of the selected dosage from the vial adapter means into the injector device.

6. A method as recited in claim 5, wherein the step of withdrawing the medication includes:

attaching the vial adapter means to the vial;

adjusting the valve arrangement to the first valve position; and operating the vial adapter means to withdraw the quantity of medication from the vial into the vial adapter means.

7. A method as recited in claim 6, wherein the step of loading the selected dosage into the injector device includes:

attaching the vial adapter means to the injector device;

adjusting the valve arrangement to the second valve position; and operating the vial adapter means to load the selected dosage into the injector device.

8. A needleless injection system, comprising:

at least one needleless injector device that is dimensioned and arranged as an integral unit to be grasped in the hand of a user, the device having a barrel portion, a gas storage portion, and an intermediate portion extending between the barrel portion and the gas storage portion;

dose dispenser means for loading the injector device with medication withdrawn from a vial having a selfsealing lid.

9. A system as recited in claim 8, wherein the dose dispenser means includes:

transporter/loader means for transporting and loading the medication; and vial coupler means for coupling the transporter/loader means to the vial for purposes of withdrawing a quantity of medication from the vial into the transporter/loader means.

10. A system as recited in claim 8, wherein the dose dispenser means includes:

vial adapter means for loading the injector device with medication withdrawn from a vial having a self-sealing lid;

the vial adapter means including injector attachment means for attaching the vial adapter means to the injector device, vial attachment means for attaching the vial adapter means to the vial, and a valve arrangement that is adjustable between a first valve position enabling withdrawal of the quantity of the medication from the vial into the vial adapter means and a second valve position enabling loading of the selected dosage from the vial adapter means into the injector device.

11. A injector device, comprising:

an integral unit dimensioned and arranged to be grasped in the hand of a user, the unit having a barrel portion, a gas storage portion, and an intermediate portion extending between the barrel portion and the gas storage portion;

the barrel portion extending from the intermediate portion to a discharge end of the barrel portion, the barrel portion defining a bore in which to load a selected dosage of a medication to be injected, and the bore extending along a bore axis from the intermediate portion to an aperture in the discharge end of the barrel portion;

the gas storage portion defining a storage compartment in which is disposed a compressed gas to be used as an energy source for ejecting the selected dosage out of the bore through the aperture; and the intermediate portion defining a chamber for receiving the compressed gas from the storage compartment, which chamber extends from the gas storage portion to the barrel portion;

the unit including gas release means for releasing the compressed gas from the storage compartment so that the compressed gas flows into the chamber and trigger means for enabling a user to actuate the gas release means; and the intermediate portion further including piston means disposed within the chamber for responding to the compressed gas in order to eject the selected dosage of medication from the barrel portion through the aperture in a high pressure jet sufficient to pass the selected dosage through the skin of the user.

12. A device as recited in claim 11, wherein:

the barrel portion is transparent to enable the user to visual discern the selected dosage within the bore.

13. A device as recited in claim 12, wherein the barrel portion includes:

a plurality of graduations disposed on the barrel portion to function as means for providing a visually discernible indication of the amount of medication within the bore.

14. A device as recited in claim 12, wherein the barrel portion includes:

an end portion extending to the discharge end; and coupling means for enabling a user to couple a dose dispenser device to the end portion for purposes of loading the selected dosage into the bore through the aperture in the discharge end.

15. A device as recited in claim 12, wherein the piston means includes:

a piston having a piston face, which piston is disposed within the chamber so that the compressed gas exerts force against the piston face when the compressed gas flows into the chamber in order to drive the piston generally toward the barrel portion; and a plunger having a plunger face, which plunger is disposed within the bore of the barrel portion so that the plunger is driven generally toward the discharge end of the barrel portion to apply force against the selected dosage in order to eject the selected dosage from the bore through the aperture when the piston is driven toward the barrel portion by the compressed gas;

the piston face having a surface area greater than the plunger face in order to increase the pressure applied to the selected dosage by the plunger face beyond the pressure that the compressed gas exerts against the piston face.

16. A device as recited in claim 15, wherein the intermediate portion includes:

vent means disposed intermediate the piston and the plunger for enabling gas to escape from a region ahead of the piston when the piston is driven by the compressed gas toward the barrel portion.

17. A device as recited in claim 11, wherein the compressed gas includes:

carbon dioxide.

18. A device as recited in claim 11, wherein the gas release means includes:

a breakable member extending through the gas storage portion from the storage compartment toward the chamber.

19. A device as recited in claim 18, wherein the breakable member includes:

a glass quill.

20. A device as recited in claim 18, wherein the trigger means includes:

a trigger member attached to the unit; and means for enabling a user to break the breakable member by operating the trigger member in order to thereby release the compressed gas from the storage compartment.

21. A device as recited in claim 20, wherein the trigger means includes:

safety means for disabling operation of the trigger.

22. A device as recited in claim 21, wherein intermediate portion includes:

discharge port means for defining a discharge port through which the compressed gas can escape from the chamber and for sealing the discharge port momentarily when the user operates the trigger member in order to delay the escape of the compressed gas from the chamber until the piston has been driven substantially all the way toward the barrel portion.

23. A injector device, comprising:

a unit having a barrel portion, a gas storage portion, and an intermediate portion extending between the barrel portion and the gas storage portion;

the gas storage portion defining a storage compartment in which is disposed a compressed gas to be used as an energy source for ejecting a selected dosage of medication out of the barrel portion; and the intermediate portion defining a chamber for receiving the compressed gas from the storage compartment;

the unit including gas release means for releasing the compressed gas from the storage compartment so that the compressed gas flows into the chamber and trigger means for enabling a user to actuate the gas release means, the gas release means including a breakable member extending through the gas storage portion from the storage compartment toward the chamber.

24. A dose dispenser device for loading an injector device with medication withdrawn from a vial having a self-sealing lid, comprising:

transporter/loader means for transporting and loading the medication; and vial coupler means for coupling the transporter/loader means to the vial for purposes of withdrawing a quantity of medication from the vial into the transporter/loader means;

the vial coupler means including cannula means for piercing the self-sealing lid of the vial; and the transporter/loader means including means for attaching the transporter/loader means to the vial coupler means in order to withdraw the quantity of the medication from the vial and for attaching the transporter/loader means to the injector device for purposes of loading the selected dosage through the aperture into the injector device.

25. A device as recited in claim 24, wherein the vial coupler means includes:

a coupler member dimensioned and arranged to be placed over the self sealing lid, which coupler member has a hollow interior extending between a closed end of the coupler member and an open end of the coupler member, the open end of which coupler member is dimensioned and arranged to fit over a lid portion of the vial so that the lid portion of the vial extends into the hollow interior of the coupler member;

a cannula having a first end portion and a second end portion, the first end portion of which is attached to the closed end of the coupler member so that the cannula extends within the hollow interior of the body member toward the open end in a position to pierce the self-sealing lid of the vial when the body member is placed over the lid portion of the vial; and means for attaching the transporter/loader means to the coupler member so that the transporter/loader means is in fluid communication with the cannula.

26. A device as recited in claim 25, further comprising:

means for locking the coupler member on the vial.

27. A device as recited in claim 26, wherein the means for locking the coupler member includes:

a slotted portion of the coupler member that is disposed between the closed end and the open end of the coupler member in a position such that the slotted portion aligns with a neck portion of the vial when the coupler member is placed over the lid portion of the vial, the slotted portion defining a pair f slots in the coupler member that are disposed opposite each other; and a collar member dimensioned and arranged to be placed through the slots and past the neck of the vial in order to engage the lid portion of the vial and thereby inhibit removal of the coupler member.

28. A dose dispenser device as recited in claim 24, wherein the transporter/loader means includes:

an elongated member having attached forward and rearward portions, the forward portion extending between forward and rearward ends of the forward portion and the rearward portion extending between forward and rearward ends of the rearward portion;

the elongated body member defining a bore extending along a bore axis from a forward end portion of the bore disposed toward the forward end of the forward portion to a rearward end portion of the bore disposed toward the rearward end of the rearward portion;

means for attaching the forward and rearward portions together so that there is a space between the rearward end of the forward portion and the forward end of the rearward portion;

a thumbwheel member disposed in the space between the forward and rearward portions, the thumbwheel member having a threaded hole axially aligned with the bore axis;

a threaded shaft disposed within the bore to function as a plunger, the threaded shaft extending within the bore through the threaded hole in the thumbwheel member to enable movement of the threaded shaft axially by rotation of the thumbwheel; and means for attaching the forward portion of the elongated member first to the vial coupler means so that the bore in the elongated member is in fluid communication with the cannula means to enable withdrawal of the quantity of medication and then to the injector device so that the bore in the elongated member is in fluid communication with the bore in the barrel portion to enable loading of the injector device.

29. A device as recited in claim 28, further comprising:

means for preventing the threaded shaft from rotating with the thumbwheel member.

30. A device as recited in claim 28, further comprising:

sealing means for maintaining a seal between the thumbwheel member and each of the forward and rearward portions of the elongated member in order to inhibit passage of contaminants into the bore in the elongated member.

31. A device as recited in claim 28, further comprising:

turn counting means for producing a human sensible signal as the thumbwheel member is rotated for purposes of enabling a user to determine the amount of medication being dispensed.

32. A device as recited in claim 28, wherein the means for attaching includes:

a threaded end portion of the elongated member that mates with a threaded portion on the vial coupler device and with a threaded portion on the injector device 33. A device as recited in claim 28, wherein:

the bore in the elongated member and the threaded shaft are dimensioned and arranged to enable a user to dispense 0.01 milliliter of medication from the bore by turning the thumbwheel approximately ninety degrees.

34. A vial adapter device for loading an injector device with medication withdrawn from a vial having a self-sealing lid, comprising:

a vial adapter body member;

injector attachment means for attaching the vial adapter body member to the injector device;

vial attachment means for attaching the vial adapter body member to the vial; and a valve arrangement that is adjustable between a first valve position enabling withdrawal of the quantity of the medication from the vial into the vial adapter body member and a second valve position enabling loading of the selected dosage from the vial adapter body member into the injector device.

35. A device as recited in claim 34, wherein the vial adapter body member includes:

attached forward and rearward portions, the forward portion extending between forward and rearward ends of the forward portion and the rearward portion extending between forward and rearward ends of the rearward portion;

the adapter body member defining a bore extending along a bore axis between a forward end portion of the bore disposed toward the forward end of the forward portion and a rearward end portion the bore disposed toward the rearward end of the rearward portion;

means for attaching the forward and rearward portions together so that there is a space between the rearward end of the forward portion and the forward end of the rearward portion;

a thumbwheel member disposed in the space between the forward and rearward portions, the thumbwheel member having a threaded hole axially aligned with the bore axis; and a threaded shaft disposed within the bore to function as a plunger, the threaded shaft extending within the bore through the threaded hole in the thumbwheel member to enable movement of the threaded shaft axially by rotation of the thumbwheel for purposes of withdrawing the quantity of medication from the vial and loading the selected dosage into the injector device.

36. A device as recited in claim 35, further comprising:

means for preventing the threaded shaft from with the thumbwheel member.

37. A device as recited in claim 35, further comprising:

sealing means for maintaining a seal between the thumbwheel member and each of the forward and rearward portions of the adapter body member to inhibit passage of contaminants into the bore in the adapter body member.

38. A device as recited in claim 35, further comprising:

turn counting means for producing a human sensible signal as the thumbwheel member is rotated for purposes of enabling a visually impaired user to determine the amount of medication being dispensed.

39. A device as recited in claim 35, wherein:

the bore in the adapter body member and the threaded shaft are dimensioned and arranged to enable a user to dispense 0.01 milliliter of medication from the bore by turning the thumbwheel approximately ninety degrees.

40. A device as recited in claim 35, wherein the vial attachment means includes:

a vial connector portion that is dimensioned and arranged to fit over a lid portion of the vial;

a cannula attached to the vial connector portion in a position to pierce the self-sealing lid of the vial when the vial connector portion is placed over the lid portion of the vial.

41. A device as recited in claim 40, further comprising:

means for locking the vial connector portion onto the vial.

42. A device as recited in claim 40, wherein the injector attachment means includes:

an injector connector portion of the adapter body member that is dimensioned and arranged to be attached to the injector device with adapter body member in fluid communication with the injector device.

43. A device as recited in claim 35, wherein the valve arrangement includes:

a valve element disposed in the forward end portion of the bore in the adapter body member for rotation about the bore axis between the first and second valve positions;

the first valve position interconnecting the bore in the adapter body member in fluid communication with the vial attachment means; and the second valve position interconnecting the bore in the adapter body member in fluid communication with the injector attachment means.

44. A device as recited in claim 35, wherein:

the vial adapter body includes a first port for providing fluid communications with the vial and a second port for providing fluid communications with the injector device; and the valve arrangement includes a valve element disposed movably within the bore, the valve element defining a passage extending between a first end facing axially toward the plunger and a second end facing radially, which valve element can be rotated between the first and second valve positions to align the second end with the first port in the first valve position and with the second port in the second valve position

* * * * *

UNITED STATES PATENT AND TRADEMARK OFFICE
CERTIFICATE OF CORRECTION

PATENT NO. : 4,913,699                    Page 1 of 2
DATED      : April 3, 1990
INVENTOR(S) : James S. Parsons It is certified that error appears in the above-identified patent and that said Letters Patent is hereby corrected as shown below:

Column 1, line 58 before "doses" insert -- device that can be loaded with a selected dosage. In addition, a dose dispenser is provided to relieve the user of the need to manipulate a hypodermic needle in order to pierce the self-sealing lid of a vial each time medication is to be withdrawn. The dose dispenser attaches permanently to the vial to provide needleless access, and it combines with the injection device in a system that greatly facilitates the self-administration of medication.
    The dose dispenser may include the combination of a transporter/loader and a vial coupler device. The transporter/loader device serves as a container in which to transport a quantity of medication and as a loading device for loading a selected dosage into the injector device, while the vial coupler device serves to couple the transporter/loader device to the vial. Alternately, the dose dispenser may take the form of a single vial adapter device. In either case, once the dose dispenser is attached to the vial, there is no exposed needle to worry about.
    In the case of the vial coupler, for example, the user attaches the vial coupler to the vial by piercing the self-sealing lid with a needle on the vial coupler. The vial coupler includes a connector arrangement for needleless coupling to the transporter/loader device so that when it is desired to withdraw a quantity of medication from the vial, the user screws the transporter/loader device onto the vial coupler without having to manipulate a needle, transfers one or more --.

Column 2, line 18 through column 2, line 46 delete the text from "device that" through "one or more".

UNITED STATES PATENT AND TRADEMARK OFFICE
CERTIFICATE OF CORRECTION

PATENT NO. :  4,913,699

DATED      :  April 3, 1990

INVENTOR(S) :  James S. Parsons

It is certified that error appears in the above-identified patent and that said Letters Patent is hereby corrected as shown below:

Column 5, line 6 change "add" to -- and --.

Column 9, line 68 change "i" to -- is --.

Column 18, line 42 change "f slots" to -- of slots --.

Column 20, line 23 after "from" insert -- rotating --.

Signed and Sealed this

Twenty-eighth Day of April, 1992

*Attest:*

HARRY F. MANBECK, JR.

*Attesting Officer*      *Commissioner of Patents and Trademarks*